United States Patent [19]

Lewenstein et al.

[11] Patent Number: 4,952,399
[45] Date of Patent: Aug. 28, 1990

[54] PHARMACEUTICAL COMPOSITION WHICH INHIBITS THE GROWTH OF A TUMOR

[75] Inventors: Ari Lewenstein, Lugano, Switzerland; Fouad K. Habib, Edinburgh, Great Britain

[73] Assignee: Cernitin SA, Barbengo, Switzerland

[21] Appl. No.: 384,054

[22] Filed: Jul. 20, 1989

Related U.S. Application Data

[63] Continuation of Ser. No. 909,833, Sep. 19, 1986, abandoned.

[30] Foreign Application Priority Data

Sep. 20, 1985 [CH] Switzerland .......................... 4089/85

[51] Int. Cl.$^5$ ............................................ A61K 35/78
[52] U.S. Cl. .................................................. 424/195.1
[58] Field of Search ..................................... 424/195.1

[56] References Cited

U.S. PATENT DOCUMENTS 3,360,437  12/1967  Carlsson .............................. 540/121

FOREIGN PATENT DOCUMENTS 0201053  12/1980  European Pat. Off. .
1025574  3/1958   Fed. Rep. of Germany .
1467750  12/1968  Fed. Rep. of Germany .
1575114  7/1969   France .
2142194  1/1973   France .

OTHER PUBLICATIONS

Chem. Abst. 71: 111220g, 1969.

Primary Examiner—John W. Rollins
Attorney, Agent, or Firm—Shenier & O'Connor

[57] ABSTRACT

Extracts which were recovered with aqueous extraction media from the pollen of plants inhibit the growth of tumor-cells and stimulate at the same time the metabolism of normal healthy cells. Said extracts of pollen which do not contain more than 5% by weight of proteins having a high molecular weight or which are completely free of such proteins of high molecular weight, are used as active ingredient of corresponding pharmaceutical preparations and they are used for treating cancer, tumors and leukemia in human beings or warm blooded animals. Living leukemia cells are rapidly killed by said extracts. The pollen extracts in question are a yellowish-white product and they usually contain, referred to the dry weight of the pollen extracts, at least 70% by weight of carbohydrates, 5–12% by weight of amino acids, peptides and/or proteinous substances and furthermore water soluble vitamines of the group B and mineral constituents.

From said yellowish-white pollen extracts a new fraction was isolated which is, compared with the pollen extracts, enriched in amino acids and/or peptides and/or proteinous substances.

11 Claims, No Drawings

PHARMACEUTICAL COMPOSITION WHICH INHIBITS THE GROWTH OF A TUMOR

This is a continuation of copending application Ser. No. 06/909,833 filed on Sept. 19, 1986 now abandoned.

BACKGROUND OF THE INVENTION

A great number of pharmaceutically active ingredients are known in the art which inhibit the growth of tumor-cells, respectively kill tumor-cells or leukaemia cells. Usually, however, said active ingredients also inhibit to a certain extent the growth of the healthy cells, however the inhibition of the growth of the healthy cells is far lower than the inhibition of the growth of the cancer cells.

The aim of the present invention was to find a pharmaceutically active ingredient which inhibits the growth of the tumor-cells and stimulates at the same time the metabolism of the normal healthy cells.

It was now quite unexpectedly found out that pollen extracts which were recovered from plant pollen by an extraction with an aqueous extraction medium, have the desired property of inhibiting the growth of tumor-cells, or even killing leukaemia cells, while said pollen extract at the same time stimulates the metabolism of normal healthy cells.

DESCRIPTION OF THE PRIOR ART

Many substances are described in the prior art which have cytostatic properties and some of said substances are already used for the chemotherapeutical treatment of cancer tumors or leukaemia. With regard to this reference is e.g. made to the publication of Pirwitz "Grundlagen und Praxis chemischer Tumorbehandlungen", Berlin, Springer, 1954.

An essential disadvantage of most of the prior art pharmaceutical compositions for treating cancer is that the active ingredients of said compositions do not only inhibit the growth of the cancer cells but that they are also to some extent toxic with regard to the healthy cells. Extended researches were made in order to develop new active ingredients for the chemotherapeutic treatment of tumors, cancer and leukaemia which do not have the above stated disadvantage.

For example there are described in the publication of B. Kellner et al. in "Naturwissenschaften", 1955, pages 582 and 583, substances having a cytostatic activity, which substances are derived from products which had already been before used for the chemotherapeutical treatment of tumors, like Nitrogen-Lost, i.e. 2,2',2"-trichlorotriethylamine, and in which derivatives the toxicity was lowered by a chemical bonding to a sugar constituent, like e.g. D-mannitol.

In the roots of certain plants of the class of the berberidaceae were found substances which inhibit the mitose which substances comprise glycosido residues and furthermore in aglucon comprising several condensed aromatic nuclei and cycloaliphatic nuclei. Said glycosides are described in the publication of A. Stoll et al. in Helv. Chim. Acta No. 37, pages 1747–1672, 1954.

Processes for the preparation of extracts from the pollen of plants are well known in the art and with regard to this we refer to the German Offenlegungsschrift No. 1 467 750, the Austrian patent No. 255 643 as well as to the U.S. Pat. No. 3 360 437. Said prior art processes make it possible to produce extracts of the pollen of plants which extracts are free or essentially free of the high molecular weight proteins of the hull of the pollen, which high molecular weight proteins might cause allergies. According to said processes the pollen were extracted with an aqueous extraction medium, thereafter a fungus of the class Mucor was added in order to digest the proteins of high molecular weight to yield proteins of low molecular weight, peptides and amino acids. After said digestion step the aqueous medium was separated from the residues of pollen and dried and the residue of pollen was further extracted with a not aqueous medium and said second extract as well recovered.

The pollen extracts produced according to said prior art process using the aqueous extraction medium and using the not aqueous extraction medium as well as mixtures of said aqueous and not aqueous pollen extracts, are available in the market and said products are used as tonics, restoratives, for accelerating the healing of wounds and broken bones, as compositions for inhibiting inflammations and for treating prostata diseases.

In the U.S. patent application Ser. No. 860 127, now U.S. Pat. No. 4,774,226, which however is not prior art, there is described a pharmaceutical composition for the prophylactic treatment of allergies, which contains as active ingredient an extract of pollen which had been recovered either using an aqueous extraction medium or using a not aqueous extraction medium or said compositions contain a mixture of said two kinds of extracts of pollen.

It was now quite unexpectedly found out that an extract of pollen of plants which was recovered by using an aqueous extraction mesium inhibits the growth of tumor-cells and stimulates the metabolism of normal healthy cells.

DETAILED DESCRIPTION OF THE INVENTION

One object of the present invention is a pharmaceutical preparation which inhibits the growth of tumor-cells and stimulates the metabolism of normal healthy cells which preparation contains as active ingredient a pollen extract recovered from plant pollen by an extraction with an aqueous extraction medium, which pollen extract contains not moe than 5% by weight of proteins having a high molecular weight or which extract is completely free of such proteins of high molecular weight.

A further object of the present invention is a process for the preparation of the pharmaceutically active ingredients of the inventive pharmaceutical preparation and according to said process the dried pollen of plants are extracted with an aqueous extraction medium, thereafter the high molecular proteins are digested by a microorganism completely or until a maximum content of not more than 5% by weight of said proteins of high molecular weight is to be found in the product, referred to the dry weight thereof, which digestion of the proteins of high molecular weight yields proteins of low molecular weight and/or peptides and/or amino acids and wherein thereafter the pollen residues are separated from the aqueous medium and the solvent evaporated from said aqueous medium by vacuum evaporation yielding a yellowish white product.

Preferred inventive pharmaceutical preparations contain as active ingredient a corresponding dried pollen extract which is a yellowish white powder and which has a water content of less than 12% by weight, referred to the total weight of said pollen extract, and which furthermore contains at least 70% by weight, referred to the total weight of the pollen extract, of carbohydrates, 5-12% by weight, referred to the total weight of the pollen extract, of amino acids and/or peptides and/or proteinous materials and furthermore the water soluble vitamines of the group B and mineral constituents.

Several kinds of tumor-cells and cancer cells were tested in order to demonstrate the growth inhibiting activity of the pollen extracts used as active ingredients of the inventive pharmaceutical preparations. Examples of such tested cells are human larynx cancer cells, human liver cancer cells, human bladder cancer cells, human prostata cancer cells, human testicle cancer cells and human breast cancer cells, as well as leukaemia cells. The cells which were alive at the beginning of the culture period and which had survived certain times of culturing were counted.

Tests for comparison were performed by culturing the specific cells in question without adding the pollen extracts of the inventive pharmaceutical compositions.

In the series of tests in which the growth inhibiting activity of the pollen extracts unto the tumor-cells or cancer cells were tested, the cell cultures were first cultivated until a certain number of cells was reached, e.g. $10^4$ cells per ml of culture medium, and thereafter a predetermined amount of the extract of pollen recovered with the aqueous extraction medium was added.

In the test cultures and also in the cultures for comparison the counting of the living cells was performed by staining with trypane blue, by which the dead cells are stained blue, while the living cells remained unstained.

It was quite unexpectedly found out that in the cultures of certain types of cancer cells immediately after the addition of the inventive extract of pollen there occurs a small increase of the number of cancer cells per ml of the culture medium. When however the treatment is continued, then after two or more days the number of the living cancer cells in the cultures decreases rapidly.

However, in the cultures of several types of the tested cancer cells immediately after the addition of the pollen extracts contained in the inventive pharmaceutical compositions there occurs a decrease of living cancer cells, compared with the cultures for comparison in which the further cultivation was made without adding said extracts.

In those cell cultures in which leukaemia cells were cultivated the extracts of pollen contained in the inventive pharmaceutical preparation exhibited a far stronger growth inhibiting activity than in cell cultures of any other of the different cancer cells. In the cultures of the leukaemia cells immediately after the addition of the extract of pollen the growth, respectively propagation of the leukaemia cells, was inhibited and beginning with the second day of the treatment, in said cultures no living leukaemia cells at all could be detected.

In the cell cultures which contained other cancer cells than leukaemia cells, the inhibition of the growth of cells, respectively propagation of cells, after the addition of the extract of pollen contained in the inventive pharmaceutical compositions was clearly evident. The results were similar for all the other kinds of cancer cells, i.e. in all tested cultures a clear inhibition of cell growth could be detected, however in none of said cultures already two days after the addition of the extract of pollen all the cancer cells were killed. This extremely strong inhibition was only to be found in the cultures of the leukaemia cells.

Furthermore, cell cultures of healthy human cells, like healthy human prostata cells or healthy human breast cells, were submitted to said test. It was clearly evident that in said cultures the living cells were not inhibited in their growth by the addition of the pollen extracts contained in the inventive pharmaceutical preparations. Contrary to this, even an increased growth of the healthy cells, compared with the corresponding cultures for comparison in which no extract of pollen was added, could be seen.

From the results of said tests there is concluded that the pollen extracts which had been recovered using aqueous extraction media contain an active ingredient or a mixture of several active ingredients which specifically inhibit the growth of cancer cells while said active ingredients at the same time stimulate the metabolism of healthy cells. Said tests furthermore demonstrate that the extracts of pollen in question have a far higher growth inhibiting activity for leukaemia cells than for any other of the tested cancer cells, because only in the cultures of the leukaemia cells within an extremely short period all living cells were killed.

A further object of the present invention is a process for the preparation of the extract of pollen used as pharmaceutically active ingredient of the inventive pharmaceutical compositions. According to said process the dried pollen of plants are extracted with an aqueous extraction medium, thereafter the proteins of high molecular weight are degraded by a microorganism completely or until a maximum content of not more than 5% by weight of said proteins of high molecular weight is to be found in the product, referred to the dry weight thereof which degradation of the proteins of high molecular weight yields proteins of low molecular weight and/or peptides and/or amino acids and wherein thereafter the pollen residues are separated from the aqueous medium and the solvent evaporated from said aqueous medium by vacuum evaporation yielding a yellowish white product.

The yellowish white product prepared according to said process is a solid product which usually has a water content of less than 12% by weight, referred to the dry weight of said product. Said product furthermore contains at least 70% by weight, referred to the dry weight of the product, of carbohydrates, 5-12% by weight, referred to the dry weight of the product, of amino acids, peptides or proteinous substances, as well as furthermore water soluble vitamines of the group B. If the product in question is burned, rather large quantities of ashes remain and, accordingly, said product has a rather high content of mineral constituents.

The chemical analysis of typical pollen extracts prepared according to the stated process are given in the table below:

| constituents | % by weight, referred to the weight of the yellowish white product |
| --- | --- |
| water | 5-10 |
| nitrogen | 2.5 |
| ashes | 4.5 |
| amino acids, peptides and proteinous substances | 6-9 |
| free phosphate | 0.8-1.4 |
| carbohydrates | 78 |

-continued

| constituents | % by weight, referred to the weight of the yellowish white product |
|---|---|
| sugar constituents | 5-10 |

The dry product furthermore contained per gram 7,5 μg of vitamine $B^2$ and 60 μg of vitamine $B^3$.

The investigation of the mineral constituents of the extract recovered with the aqueous extraction medium according to the above stated process gave the following results:

| constituent | quantity in ppm |
|---|---|
| Ca | 56 |
| P | 58 |
| Mg | 11 |
| Na | 250 |
| Fe | 18 |
| Zn | 2.3 |
| Cu | 5 |
| Al | 12 |

Also the sugar constituents of the extract were investigated and there could be found therein arabinose, galactose, mannose and glucose in amounts of traces until 4% by weight or even in higher quantities.

The activity of the extract of plant pollen recovered with the aqueous extraction medium to stimulate the metabolism of healthy cells was determined by performing in vitro tests. This was done with the cyclic adenosine-monophosphate-essay which will be abbreviated further as c-AMP-essay. Said test was performed with highly purified leydig-cells which were present in the culture medium in a cell concentration of $10^5$ cells/ml of the culture medium. The c-AMP-essay is a test according to a deficital model, in which preaged cells are stimulated with the peptidal hormone hcg and are essayed radioimmunologically for their c-AMP-production. The ageing of the cells was performed in this case by ageing them for 24 hours at a temperature of 6° C. If a product is added to the cell culture and said product stimulates the c-AMP-production, then this shows that the product in question has to contain active ingredients which compensate the deficit, respectively deficiency which had been produced by the ageing process. The product in question, accordingly, has to contain active ingredients which result in a stimulation of the metabolism of the cells.

The extract of pollen recovered with the aqueous extraction medium which is the active ingredient of the inventive pharmaceutical composition resulted in a clear stimulation of the c-AMP-production of the tested cells, compared with the corresponding cell cultures for comparison which were cultivated further without the adding of such extracts of pollen.

Said tests were also performed with cell cultures which did not contain highly purified leydig-cells but human prostata cells. In this case the results were about the same.

The aqueous extraction media which are used to prepare the extract of pollen are preferably mixtures of a larger part of water and a smaller part, referred to the weight of the solvent mixture, of an organic solvent which is completely water miscible. Examples for such organic solvents are lower alcohols or lower ketones, as for example ethanol or acetone. Usually an aqueous extraction medium is used which has a content of 2-30% by weight of the completely water miscible organic solvent and wherein the remainder up to 100% by weight is water, preferably distilled water.

Examples for aqueous extraction media which can be used are a 20% by weight aqueous solution of ethanol or a 5% by weight aqueous solution of acetone.

Usually the dried pollen are treated with said aqueous extraction medium for one day to three days at room temperature or a temperature of up to 35° C. and the pollen are stirred in said extraction medium.

After said preextraction treatment microorganisms are added to said mixture of pollen and aqueous extracting medium and the pollen are stirred in said medium in the presence of the microorganisms for further 36-60 hours at a temperature in the range of 15°-35° C. During this time the outer hulls of the pollen are metabolized by the microorganisms. The microorganisms degradate the proteins of high molecular weight yielding proteinous substances of low molecular weight or peptides or free amino acids or mixtures of such components.

The pollen used for performing the above stated extraction process contain proteins of high molecular weight, specially in the hull of said pollen, and said proteins of high molecular weight can cause allergies if a person sensitive to said allergy comes into contact with the product in question. Said proteins of high molecular weight are therefore metabolized by the used microorganisms at least to such a degree that the product obtained after said fermentation is no longer able to provoke allergies.

The microorganisms used for performing said fermentation are preferably fungi. Fungi which are advantageously used for said purpose are fungi of the class of Mucor. As examples of such fungi which can be used for metabolizing the proteins of high molecular weight, reference is made to the following fungi:

*Mucor glomerata; Mucor luteus; Mucor mucedo; Mucor flavus, Mucor corticolus, Mucor brunneus, Mucor hiemalis* or *Mucor alpinus.*

After said fermentation treatment the residues of the pollen are separated from the aqueous extraction medium, preferably by performing a filtration. The resulting filtrate is a clear solution. From said filtrate the aqueous medium containing the water miscible organic solvent, is removed by evaporating applying a vacuum. The dry residue after said evaporation is a yellowish white product.

Said yellowish white product is the mixture of active ingredients which usually is composed of the constituents named before, i.e. the organic substances, the vitamines and the mineral constituents. Said dry residue is the active ingredient of the inventive pharmaceutical compositions for inhibiting the growth of tumor-cells and stimulating the metabolism of the healthy cells.

With regard to the selection of the plant pollen in question and further details of the extraction process performed with the aqueous extraction medium, reference is made to what is already disclosed in the German Offenlegungsschrift 1 467 750, the Austrian patent No. 255 643 and the U.S. Pat. No. 3,360,437. Furthermore the process for the preparation of pollen extracts using aqueous extraction media and furthermore also processes for the preparation of pollen extracts using not aqueous extraction media, are in detail described in the elder not yet published U.S. patent application Ser. No. 860,127. The tests with the cell lines of human cancer cells and healthy human cells were as well performed with the pollen extracts which had been recovered by the extraction with the not aqueous extraction medium. Said tests, however, showed that the extracts of pollen which had been recovered using the not aqueous extraction medium, did not inhibit the growth of the human cancer cells in the stated cell cultures.

From the pollen extracts recovered with the aqueous extraction medium, which were a yellowish white product, there were isolated fractions which are enriched in amino acids and/or peptides and/or proteinous substances. Said fractions are a new product.

A further object of the present invention accordingly is a new fraction of a pollen extract recovered with the aqueous extraction medium, which fraction is enriched in amino acids and/or peptides and/or proteinous substances, compared with the pollen extract from which said fraction was isolated, and said fraction furthermore contains not more than 5% by weight, referred to the dry weight of said fraction, of proteins having a high molecular weight or said fraction is completely free of proteins of high molecular weight.

A further object of the invention is a process for isolating a fraction which is enriched in amino acids and/or peptides and/or proteinous substances from the pollen extracts which had been recovered with the aqueous extraction medium.

According to one embodiment of the process for isolating the fraction enriched in amino acids and/or peptides and/or proteinous substances the yellowish white powder is submitted to a chromatographic separation using a column and thereby those fractions are recovered in which amino acids and/or peptides and/or proteinous substances can be detected by the ninhydrine test. According to said process the yellowish white powder is dissolved in a suitable solvent, preferably in water or a mixture of water and an organic solvent which is completely water miscible. Said solution is then submitted to the chromatographic separation by applying it to a corresponding column. It is advantageous to perform said chromatographic separation by using a column which is filled with sephadex. Those fractions in which with the ninhydrine test the presence of amino acids and/or peptides and/or proteinous substances could be detected were recovered and the solvent was evaporated applying a vacuum. The remaining dry product is the fraction enriched in amino acids and/or peptides and/or proteinous substances.

According to a further embodiment of the process for isolating the fraction enriched in amino acids and/or peptides and/or proteinous substances from the yellowish white powder, said powder was first dissolved in water and to said solution there was added an organic solvent which is completely water miscible and optionally, furthermore, an organic acid. Said water miscible organic solvent lowers the solubility of the peptides and/or proteinous substances and/or amino acids in the aqueous solution and said substances are precipitated. The precipitate is then isolated and dried.

Examples for organic solvents which are completely water miscible and which accordingly can be used for performing said precipitation are lower alcohols or lower ketones. The organic acids which advantageously are as well added to the aqueous solution are preferably aliphatic carboxylic acids or aromatic carboxylic acids, as for example benzoic acid.

According to an embodiment of said process for precipitating the fraction which is enriched in amino acids and/or peptides and/or proteinous substances, the yellowish white product which had been recovered from the pollen of plants by the extraction with the aqueous extraction medium, is dissolved in water, preferably in distilled water. To said solution there is then added acetone and furthermore benzoic acid. The precipitate which is formed is enriched in amino acids, proteinous substances and peptides, referred to the yellowish white powder from which the aqueous solution had been prepared.

Furthermore there was isolated by a microgradient-gel-electrophoresis from said fractions enriched in amino acids and/or peptides and/or proteinous substances a product containing peptides which had a molecular weight in the range of 650-750. It is believed that said product comprises 6-8 amino acid moieties. According to said microgradient-gel-electrophoresis there was furthermore isolated a peak having a molecular weight of about 700. It is believed that the product of said isolated peak is a protein having 7 amino acid moieties, i.e. a heptapeptide.

Further tests will be performed in order to determine the pharmacological activity of the fractions enriched in amino acids and/or peptides and/or proteinous substances which had been isolated from the pollen extracts recovered with the aqueous extraction medium.

The present invention shall be further illustrated with the following examples. All the tests which were performed with cancer cells, tumor cells and healthy cells were performed with an extract of plant pollen prepared according to the process of example 1 or prepared according to a similar extraction process. The fractions which are enriched in proteinous substances, peptides and amino acids, which were prepared according to example 2 and example 3 are new products. Until now, however, said products were not yet tested as to their activity for inhibiting the growth of cancer cells.

EXAMPLE 1

120 kg of pollen of rye, having the scientific latin denomination *secale cereale* were treated with 600 kg of a solution of 20 mol percent of ethanol in water. The pollen were stirred in said solution for 48 hours at a temperature in the range of 30°-32° C. After said pretreatment step the fungus *Mucor alpinus* was added and the pollen stirred in said aqueous medium for further 20-30 hours at a temperature of 30° C.

The aqueous medium is isolated from the pollen residue by filtration. The filtrate is a clear solution. Said clear solution was sterilized by performing a sterilizing filtration and from the filtrate the solvent was evaporated by applying a vacuum. This yielded the dry extract of the pollen of rye and said product was a yellowish white powder.

Said yellowish white powder was used for preparing the pharmaceutical preparations which inhibit the growth of the tumor cells and stimulate the metabolism in the healthy cells.

Said pharmaceutical preparations can be preparations for a topic administration, an oral administration or an administration by injection, like e.g. corresponding lotions, ointments, pills, capsules or injectable solutions.

EXAMPLE 2

The product prepared according to the process of example 1 was dissolved in water and this yielded a clear solution. Thereafter to said solution acetone and benzoic acid were added. The acetone was added drop by drop and thereby a precipitate was formed. The acetone was added in such a quantity until a further drop of acetone added did no longer result in the formation of further precipitate.

The precipitate was isolated from the liquid medium, for example by filtration or by removing the solvent by suction. The isolated precipitate was then dried under vacuum.

From 100 parts by weight of the yellowish white product prepared according to the process of example 1 there were isolated 60 parts by weight of the dried precipitate.

The mother liquor from which the precipitate was isolated was essentially free or completely free from proteinous materials or peptides. Said mother liquor was discarded. The precipitate accordingly was enriched, compared with the yellowish white power from which it had been prepared, in peptides, amino acids and proteinous substances.

EXAMPLE 3

The fraction enriched in peptides, proteinous materials and amino acids, prepared according to the process of example 2 was submitted to the microgradient-gel-electrophoresis. The peak having a molecular weight of about 700 Da was isolated. 100 parts by weight of the yellowish white powder prepared according to example 1 yielded about one part by weight of the peptides having a molecular weight of about 700.

EXAMPLE 4

In the present example the activity of the active ingredients of the inventive pharmaceutical preparation to inhibit the growth of tumor cells was tested by treating the cell culture of leukaemia cells with the extract of pollen which had been recovered using the aqueous extraction medium.

At the beginning of the test each of the cell cultures contained $4 \times 10^4$ leukaemia cells per ml of the culture medium. In the cultures for comparison, to which no extract of pollen was added, the number of living leukaemia cells increased from the first day of the test until the fourth day of the test from $4 \times 10^4$ leukaemia cells per ml of $5.2 \times 10^5$ cells per ml.

In the cell cultures to which the extract of pollen has been added in an amount of 1 mg/ml of culture, at the end of the first day of the treatment, the number of the living leukaemia cells had decreased from $4 \times 10^4$ living cells per ml to $4 \times 10^3$ living cells per ml. Beginning with the second day of said treatment no more living cells at all could be detected in said cultures.

In a second series of cell cultures to the cultures the extract of pollen was added in a quantity of 4 mg/ml. In this case already on the first day of the treatment the number of the living leukaemia cells decreased from $4 \times 10^4$ living cells per ml to $2 \times 10^3$ living cells per ml. Also in this case, starting from the second day of the treatment, no living leukaemia cells at all could be found in the cell cultures.

The corresponding test results are stated in the table below:

| days after the beginning of the treatment | number of living leukaemia cells per ml after the pollen extract has been added to the cultures in a quantity of | | |
|---|---|---|---|
| | 0 | 1 mg/ml | 4 mg/ml |
| 1 | $4.0 \times 10^4$ | $4 \times 10^3$ | $2 \times 10^3$ |
| 2 | $6.0 \times 10^4$ | 0 | 0 |
| 3 | $2.2 \times 10^5$ | 0 | 0 |
| 4 | $5.2 \times 10^5$ | 0 | 0 |

Similar cell cultures were prepared, however in said cell cultures not leukaemia cells but normal human white blood cells were tested. Also in this case to the cell cultures for comparison no pollen extract was added and said cultures were cultivated for three further days.

To one series of cell cultures there was added 1 mg/ml of the culture of the extract of pollen and to another series of cultures the extract of pollen was added in a quantity of 4 mg/ml of the culture and said cultures were as well further cultivated.

All the cell cultures were further cultivated for three days. In all cultures, also in the cultures for comparison, a small reduction of the number of living cells was to be found during the three days of cultivation. However nearly no difference in the number of living cells could be detected between the cultures for comparison and the cultures to which the cell extract had been added in a quantity of 1 ml/ml respectively 4 mg/ml of culture medium.

It can be seen from said test results that the pollen extract recovered with the aqueous extraction medium which is the active ingredient of the inventive pharmaceutical preparations is able to kill selectively the leukaemia cells, that said extract however does not at all hinder the growth of the healthy white blood cells.

EXAMPLE 5

In said example cell cultures of human prostata cancer cells and human testicle cancer cells were tested.

In the same way as described in example 4 in the cell cultures for comparison the further cultivation was performed without adding a pollen extract while in one series of cell cultures the further cultivation was performed after 1 mg/ml of the cell culture of the extract of pollen prepared according to example 1 was added and in a further series of cell cultures the further cultivation was performed after 4 mg/ml of the cell culture of the extract of pollen prepared according to example 1 had been added.

At the beginning of the test each cell culture contained $4.4 \times 10^4$ cells of human prostata cancer cells per ml of cell culture. In the cultures for comparison the living cells of human prostata cancer increased from $4.4 \times 10^4$ cells per ml to $1.2 \times 10^5$ cells per ml until the fourth day of cultivation.

In the cell cultures which were further cultivated after 1 mg/ml of the extract of pollen had been added, the number of living cancer cells also increased slightly, but the increase of the cell number was far lower than in the group for comparison. In said cultures the number of living cancer cells increased from $4.4 \times 10^4$ cells per ml to $7.6 \times 10^4$ cells per ml on the fourth day of further cultivation.

In the cell cultures which were further cultivated after 4 mg/ml of culture of the extract of pollen prepared according to example 1 had been added, a clear diminuation of the number of living cells occurred. In said cell culture the number of living human prostata cancer cells decreased from $4.4 \times 10^4$ cells per ml after the addition of the pollen extract to $6.0 \times 10^3$ living cells on the fourth day after said extract had been added.

The results of said tests are stated in the following table.

| Cell cultures of human prostata cancer cells | | | |
|---|---|---|---|
| days after the beginning of the treatment | number of the living human prostata cancer cells per ml after the addition of the extract of pollen in a quantity of | | |
| | 0 | 1 mg/ml | 4 mg/ml |
| 1 | $4.4 \times 10^4$ | $3.8 \times 10^4$ | $4.2 \times 10^4$ |
| 2 | $6.0 \times 10^4$ | $3.2 \times 10^4$ | $3.6 \times 10^4$ |
| 3 | $1.0 \times 10^5$ | $4.4 \times 10^4$ | $1.2 \times 10^4$ |
| 4 | $1.2 \times 10^5$ | $7.6 \times 10^4$ | $6.0 \times 10^3$ |

In the cell cultures in which human testicle cancer cells were cultivated, in the group for comparison until the fourth day of further cultivation a small decrease of the number of living cancer cells was observed.

In the cell cultures in which the further cultivation was performed after 1 mg/ml of culture of the pollen extract had been added, the number of living cancer cells in said cultures was far more lowered than in the group for comparison and a still higher decrease of the living cancer cells was to be found in those cell cultures to which the pollen extract had been added in a quantity of 4 mg/ml.

Similar tests were performed with cell cultures of human larynx cancer cells, human liver cancer cells, human bladder cancer cells and human breast cancer cells. The results were similar to the results which were to be found in the cell cultures of human prostata cancer cells.

What is claimed is:

1. A method of inhibiting the growth of tumor-cells and stimulating the metabolism of normal healthy cells including the step of administering a preparation containing as active ingredient a pollen extract recovered from plant pollen by an extraction with an aqueous extraction medium, which pollen extract contains not more than 5% by weight of proteins having a high molecular weight.

2. A method as claimed in claim 1 in which said preparation contains as active ingredient a corresponding dried pollen extract which is a yellow to white powder, has a water content of less than 12% by weight and which contains, referred to the total weight of said pollen extract, at least 70% by weight of carbohydrates, 5 to 12% by weight of materials selected from the group consisting of amino acids, peptides and proteinous materials and furthermore water soluble vitamines of the group B.

3. A method as claimed in claim 1 in which said preparation contains as active ingredient the fraction of the extract of pollen recovered with the aqueous extraction medium which is enriched in its content of materials selected from the group consisting of amino acids, peptides and proteinous materials.

4. A method as claimed in claim 1 in which said extract is completely free of said proteins of high molecular weight.

5. A method as in claim 1 in which said preparation is produced by a process wherein the dried pollen of plants are extracted with an aqueous extraction medium, thereafter high molecular proteins are degraded by a microorganism completely or until a maximum content of not more than 5% by weight of said proteins of high molecular weight is to be found in the product, referred to the dry weight thereof which degradation of the proteins of high molecular weight yields products selected from the group consisting of proteins of low molecular weight peptides and amino acids and wherein thereafter the pollen residues are separated from the aqueous medium and the solvent evaporated from said aqueous medium by vacuum evaporation yielding a yellowish white product.

6. A method as in claim 5 in which said preparation producing process comprises enriching a fraction isolated from the yellowish white product in substances selected from the group consisting of amino acids, peptides and proteinous materials, which fraction, however, contains not more than 5% by weight, referred to the dry weight of said product of proteins having a high molecular weight or which is completely free of such proteins of high molecular weight, by dissolving the yellowish white product in water, mixing it with a completely water miscible organic solvent, and wherein the formed precipitate is isolated and dried, which precipitate is enriched in amino acids, peptides or proteinous substances.

7. A method as in claim 6 wherein said preparation producing process comprises the precipitation of the substances selected from the group consisting of amino acids, peptides and proteinous substances by adding to the aqueous solution acetone and benzoic acid.

8. A method as in claim 6 in which said water miscible organic solvent is a lower alcohol or a lower ketone and in which an organic acid is added.

9. A method as in claim 5 in which said preparation producing process comprises enriching a fraction isolated from the yellowish white powder in substances selected from the group consisting of amino acids, peptides and proteinous substances is isolated by submitting said powder to a chromatographic separation using a column, and by collecting the fractions in which amino acids and/or peptides and/or proteinous substances can be detected by the nin-hydrine test.

10. A method of inhibiting the growth of tumor cells and stimulating the metabolism of normal healthy cells including the step of administering a mixture containing substances from the groups consisting of amino acids, proteinous substances and peptides which is a corresponding fraction isolated from an extract of plant pollen which has been recovered using an aqueous extraction medium.

11. Process for treating cancer, tumors and leukemia in human beings or warm blooded animals by administering to them an extract of a pollen of plants which had been recovered from the plant pollen by using an aqueous extraction medium, which pollen extract contains not more than 5% by weight of proteins having a high molecular weight.

* * * * *